US011311556B2

(12) United States Patent
Jindal et al.

(10) Patent No.: US 11,311,556 B2
(45) Date of Patent: Apr. 26, 2022

(54) TOPICAL DUTASTERIDE EMULSIONS FOR TREATING ENDOCRINE THERAPY-INDUCED ALOPECIA

(71) Applicant: Varsona Therapeutics, Inc., San Francisco, CA (US)

(72) Inventors: Vinay Kumar Jindal, San Francisco, CA (US); Manu Gujrati, San Francisco, CA (US); Mary Angelica Oba Magsombol-Karaan, Rohnert Park, CA (US)

(73) Assignee: Varsona Therapeutics, Inc., San Francisco, CA (US)

( * ) Notice: Subject to any disclaimer, the term of this patent is extended or adjusted under 35 U.S.C. 154(b) by 0 days.

(21) Appl. No.: 16/890,044

(22) Filed: Jun. 2, 2020

(65) Prior Publication Data
US 2021/0353643 A1     Nov. 18, 2021

Related U.S. Application Data

(60) Provisional application No. 63/023,989, filed on May 13, 2020.

(51) Int. Cl.
| | | |
|---|---|---|
| *A61K 31/568* | (2006.01) | |
| *A61K 9/107* | (2006.01) | |
| *A61K 9/00* | (2006.01) | |
| *A61P 17/14* | (2006.01) | |
| *A61K 47/14* | (2017.01) | |
| *A61K 47/08* | (2006.01) | |
| *A61K 47/10* | (2017.01) | |

(52) U.S. Cl.
CPC .......... *A61K 31/568* (2013.01); *A61K 9/0014* (2013.01); *A61K 9/107* (2013.01); *A61K 47/08* (2013.01); *A61K 47/10* (2013.01); *A61K 47/14* (2013.01); *A61P 17/14* (2018.01)

(58) Field of Classification Search
CPC .... A61K 31/568; A61K 9/0014; A61K 9/107; A61K 47/08; A61K 47/10; A61K 47/14; A61K 9/06; A61P 17/14
See application file for complete search history.

(56) References Cited

U.S. PATENT DOCUMENTS

| | | | |
|---|---|---|---|
| 4,339,276 A | 7/1982 | Yokoyama et al. | |
| 4,950,475 A | 8/1990 | Vishnupad et al. | |
| 5,030,374 A | 7/1991 | Tranner | |
| 5,422,361 A | 6/1995 | Munayyer et al. | |
| 5,914,334 A | 6/1999 | Charu | |
| 7,854,940 B2 | 12/2010 | Ciccognani et al. | |
| 10,441,567 B2 | 10/2019 | Zhi | |
| 2002/0035070 A1* | 3/2002 | Gardlik | A61Q 3/00 514/23 |
| 2003/0191035 A1 | 10/2003 | Verboom et al. | |
| 2004/0167046 A1 | 8/2004 | Lukenbach et al. | |
| 2006/0204588 A1* | 9/2006 | Liversidge | A61K 9/146 424/490 |
| 2007/0202180 A1 | 8/2007 | Liversidge et al. | |
| 2008/0260864 A1* | 10/2008 | Dascalu | A61K 8/23 424/685 |
| 2010/0048598 A1* | 2/2010 | Kandavilli | A61K 9/12 514/275 |
| 2011/0212167 A1 | 9/2011 | Ali et al. | |
| 2014/0079686 A1 | 3/2014 | Barman et al. | |
| 2014/0322148 A1 | 10/2014 | Jackson | |
| 2015/0216986 A1 | 8/2015 | Pohlmann et al. | |
| 2019/0022000 A1 | 1/2019 | Tamarkin et al. | |
| 2019/0091149 A1 | 3/2019 | Tamarkin et al. | |
| 2019/0224109 A1 | 7/2019 | Florence et al. | |
| 2020/0147071 A1 | 5/2020 | Jindal | |

FOREIGN PATENT DOCUMENTS

| | | |
|---|---|---|
| EP | 0027286 A2 | 4/1981 |
| WO | WO-2018/013142 A1 | 1/2018 |
| WO | WO-2019/012353 A1 | 1/2019 |
| WO | WO2019012353 * | 1/2019 |

OTHER PUBLICATIONS

Cetostearyl alcohol (PubChem CID 62238 p. 1-22) [online], Retrieved from the internet, Retrieved on Dec. 23, 2020, <url:https://pubchem.ncbi.nlm.nih.gov/compound/Cetostearyl-alcohol> (Year: 2010).*
Ethylene glycol monostearate (PubChem 24762, p. 1-30) [online], Retrieved from the internet, Retrieved on Dec. 23, 2020, <url: https://pubchem.ncbi.nlm.nih.gov/compound/24762> (Year: 2005).*
Bhatia et al., "Tamoxifen-loaded liposomal topical formulation arrests hair growth in mice", Br J Dermatol. 163(2):412-5 (2010).
Clark et al., "Marked Suppression of Dihydrotestosterone in Men with Benign Prostatic Hyperplasia by Dutasteride, a Dual 5alpha-Reductase Inhibitor", J Clin Endocrinol Metab. 89(5): 2179-2184 (2004).
Farshi et al., "A randomized double blind, vehicle controlled bilateral comparison study of the efficacy and safety of finasteride 0.5% solution in combination with intense pulsed light in the treatment of facial hirsutism," J Cosmet Laser Ther. 14(4):193-9 (2012).
Frank, Chapter 136: Pituitary Pars Intermedia Dysfunction. *Robinson's Current Therapy in Equine Medicine, Seventh Edition*. Sprayberry and Robinson, Elsevier, 574 (2015).
Freites-Martinez et al., "Endocrine Therapy-Induced Alopecia in Patients With Breast Cancer," JAMA Dermatol. 154(6):670-5 (2018) (12 pages).
Gallicchio et al., "Aromatase inhibitor therapy and hair loss among breast cancer survivors," Breast Cancer Res Treat. 142(2): 435-43 (2013).

(Continued)

*Primary Examiner* — Sahar Javanmard
(74) *Attorney, Agent, or Firm* — Clark & Elbing LLP

(57) ABSTRACT

The invention features topical dutasteride emulsions for local delivery to the dermis of a subject suffering from hair loss, such as hair loss secondary to endocrine therapy in patients with breast cancer.

1 Claim, 1 Drawing Sheet

(56) References Cited

OTHER PUBLICATIONS

Herskovitz et al., "Female Pattern Hair Loss," Int J Endocrinol Metab. 11(4):e9860 (2013) (8 pages).
Jain et al., "Potential targets in the discovery of new hair growth promoters for androgenic alopecia," Expert Opin Ther Targets. 18(7):787-806 (2014).
Lindner et al., "Hair shaft abnormalities after chemotherapy and tamoxifen therapy in patients with breast cancer evaluated by optical coherence tomography," Br J Dermatol. 167(6): 1272-8 (2012).
Olsen et al., "The importance of dual 5alpha-reductase inhibition in the treatment of male pattern hair loss: Results of a randomized placebo-controlled study of dutasteride versus finasteride," J Am Acad Dermatol. 55(6):1014-23 (2006).
Rowland et al., "Androgenic alopecia: the risk-benefit ratio of Finasteride," J Mind Med Sci. 5(1):1-6(2018) (8 pages).
Saggar et al., "Alopecia With Endocrine Therapies in Patients With Cancer," The Oncologist, 18(10):1126-34 (2013).
Sawaya et al., "Different Levels of 5alpha-Reductase Type I and II, Aromatase, and Androgen Receptor in Hair Follicles of Women and Men with Androgenetic Alopecia," J Invest Dermatol. 109(3):296-300 (1997).
Shapiro, "Clinal Practice. Hair Loss in Women," N Engl J Med. 357(16):1620-30 (2007).
Wang and Lu, "Protection Against Chemotherapy-Induced Alopecia," Pharm Res. 23(11):2505-14 (2006).
FDA Label for Avodart (19 pages) (2008).
Karatas et al., "Management of hair loss associated with endocrine therapy in patients with breast cancer: an overview," SpringerPlus 5:585 (2016).
Office Action for U.S. Appl. No. 16/676,657, dated Jul. 31, 2020 (36 pages).
Response to Non-Final Office Action and Declaration of Manu Gujrati, M.D. Under 37 C.F.R. § 1.132 for U.S. Appl. No. 16/676,657, filed Nov. 2, 2020 (34 pages).
Rozner et al., "Safety of 5α-reductase inhibitors and spironolactone in breast cancer patients receiving endocrine therapies," Breast Cancer Res Treat. 174(1): 15-26 (2019).
Rugo et al., "Alopecia related to systemic cancer therapy," UpToDate. (26 pages) (2020).
All et al., "Preparation, characterization and stability study of dutasteride loaded nanoemulsion for treatment of benign prostatic hypertrophy," Iran J Pharm Res. 13(4):1125-40 (2014).
Lubrizol LifeSciences. "Promulgen D Nonionic Emulsifier." Technical Data Sheet, published Nov. 5, 2014 (2 pages).
The Concise Oxford Dictionary (Tenth Edition). Ed. J. Pearsall. "Emulsion". Oxford University Press, 1999, p. 468.
Final Report on the Safety Assessment of Steareth-2,-4,-6,-7,-10,-11,-13,-15, and-20. (1988). Journal of the American College of Toxicology, 7(6), 881-910.
Andersen, F. A. (1999). Final Report on the Safety Assessment of Ceteareth-2, -3, -4, -5, -6, -7, -8, -9, -10, -11, -12, -13, -14, -15, -16, -17, -18,-20,-22,-23,-24,-25,-27, -28, -29, -30, -33, -34, -40, -50, -55, -60, -80, and -100. International Journal of Toxicology, 18(3_suppl), 41-49.
Final Rejection for U.S. Appl. No. 16/676,657, dated Mar. 12, 2021 (28 pages).
International Search Report and Written Opinion for International Application No. PCT/US2021/032250, dated Sep. 14, 2021 (10 pages).
Response to Final Office Action for U.S. Appl. No. 16/676,657, filed Sep. 13, 2021 (7 pages).
Notice of Allowance for U.S. Appl. No. 16/676,657, dated Jan. 11, 2022 (13 pages).

\* cited by examiner

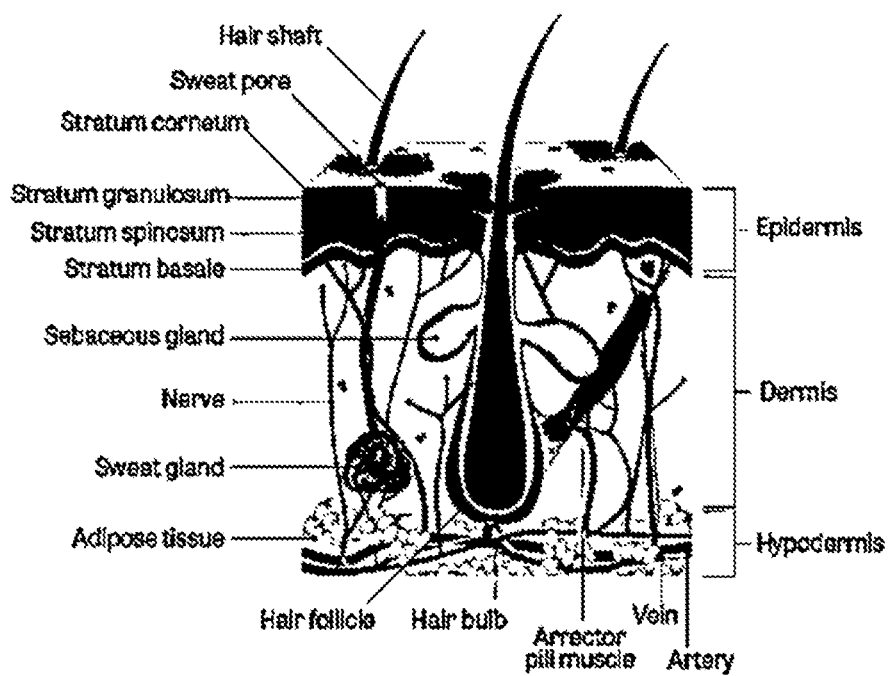

TOPICAL DUTASTERIDE EMULSIONS FOR TREATING ENDOCRINE THERAPY-INDUCED ALOPECIA

FIELD OF THE INVENTION

The invention features topical compositions for locally modulating hair growth or ameliorating hair loss and the treatment of various types of alopecia, such as hair loss secondary to endocrine therapy in patients with breast cancer (Endocrine Therapy-Induced Alopecia or ETIA).

BACKGROUND OF THE INVENTION

Hair loss or alopecia is a common and embarrassing problem for many people. One of the most frequent types of alopecia is androgenetic alopecia, which is a common form of hair loss in both men and women (e. g., in men, "male-pattern baldness").

Another common form of alopecia is hair loss secondary to endocrine therapy in patients with breast cancer (Endocrine Therapy-Induced Alopecia or ETIA). Selective Estrogen Receptor Modulators (SERMs) and Aromatase Inhibitors (AIs) currently hold an important place as adjuvant endocrine therapy for patients with early invasive or non-invasive, and/or advanced metastatic, hormone receptor-positive breast cancer. A substantial portion of the patients using SERMs, such as tamoxifen, for many years has reported hair loss or hair thinning. See Gallicchio, L. et al. "Aromatase inhibitor therapy and hair loss among breast cancer survivors." *Breast Cancer Res Treat* (2013) 142: 435-43. A retrospective questioning of patients with breast cancer regarding hair loss has revealed that approximately 34% of patients receiving endocrine therapy experience hair loss or thinning. See id. The psychosocial importance of alopecia resulting from cancer therapies cannot be understated. Approximately 58% of women receiving treatment for breast cancer state that alopecia is one of the most traumatic adverse events (AEs) during their treatment, with 8% indicating they would reject treatment because of this reaction alone. See Saagar, V. et al. "Alopecia with Endocrine Therapies in Patients with Cancer." *Oncologist* (2013) 18(10): 1126-34. Decreased Quality of Life (QoL), social activity, self-esteem, and body image are all associated with hair loss. See Wang, J. et al. "Protection Against Chemotherapy-Induced Alopecia." *Pharm Res.* (2006) 23(11): 2505-14 and Shapiro, J. "Hair Loss in Women." *N Engl J Med* (2007) 357(16) 1620-30. These findings have been attributed to the severe alopecia that develops during treatment with cytotoxic agents. Endocrine Therapy-Induced Alopecia (ETIA) that occurs during treatment with endocrine agents is often, but not always of lower severity; however, ETIA can last for the duration of treatment (typically 5-10 years) which heightens and extends the impact on patients' QoL. ETIA has a significant negative impact on the QoL and often results in depression, anxiety and dissatisfaction with one's appearance and low self-esteem.

The properties of hair growth and the underlying mechanisms of androgenetic alopecia (AGA) may help explain why SERMs and AIs cause ETIA. Animal (mice) models treated with a tamoxifen-loaded gel experienced arrested hair growth, with no growth persisting even after discontinuation of this treatment. See Bhatia, A. et al. "Tamoxifen-loaded liposomal topical formulation arrests hair growth in mice." *Br J Dermatol* (2010) 163(2): 412-15. Further, the affected hair follicles were arrested in the telogen phase. See id. Alopecia related to tamoxifen has been shown to exhibit a distribution similar to that of female AGA, primarily affecting the crown and frontal scalp. See Linder, J. et al. "Hair shaft abnormalities after chemotherapy and tamoxifen therapy in patients with breast cancer evaluated by optical coherence tomography." *Br J Dermatol* (2012) 167(6): 1272-78. Both men and women with AGA have lower levels of aromatase in hair follicles located within the frontal region of the scalp (see Sawaya, M. and Price, V. "Different Levels of 5'-Reductase Type I and II, Aromatase, and Androgen Receptor in Hair Follicles of Women and Men with Androgenetic Alopecia." *J Invest Dermatol* (1997) 109(3): 296-300.); therefore, it is possible that AIs mimic the hereditary deficiency typically seen in AGA.

Researchers have attempted several treatment regimens to address different forms of alopecia with mixed results. For example, vasodilators such as potassium channel agonists including minoxidil and minoxidil derivatives such as diaminopyrimidine oxide; and an oral formulation of inhibitors for 5-α reductase enzyme that converts testosterone to dihydrotestosterone (DHT) for the treatment of alopecia. Use of such oral formulations of such inhibitors like oral finasteride has resulted in mixed success and with a risk of adverse side effects.

Avodart® (dutasteride) has been shown to be safe and effective for oral use through both extensive nonclinical testing and data obtained from over 18 years of clinical use. Dutasteride reduces circulating levels of DHT by inhibiting both type 1 and type 2 5α-reductase isoenzymes that are responsible for the conversion of testosterone to DHT, which is known to be the most potent natural androgen in the human body. DHT is believed to potently regulate the transcription of androgen-sensitive genes within the follicle, thereby affecting hair growth. See Jain, R. and De-Ekanumkul. "Potential targets in the discovery of new hair growth promoters for androgenic alopecia." *Expert Opin Ther Targets* (2014) 18(7): 787-086. Therefore, systemic treatment with anti-5α-reductase agents (such as oral Avodart® (dutasteride) soft gelatin capsules, 0.5 mg) has been shown to treat hair loss on the scalp in both men and women. The fact that patients with deficiency of congenital 5α-reductase enzyme activity rarely experience AGA (see Herskovitz, I. and Tosti, A. "Female Pattern Hair Loss." *Int J Endocrinol Metab* (2013) 11(4): e9860 (published online Oct. 21, 2013)), and that those patients using 5α-reductase enzyme inhibitors have a significant improvement in hair loss (see Olsen, E. et al. "The importance of dual 5α-reductase inhibition in the treatment of male pattern hair loss: Results of a randomized placebo-controlled study of dutasteride versus finasteride." *J Am Acad Dermatol* (2006) 55(6): 1014-23) are the objective preliminary evidence of this proposed indication.

Oral finasteride and oral dutasteride are two of the most widely known and frequently used 5α-reductase inhibitors available today. Both drugs are designed to inhibit the conversion of testosterone into DHT. DHT is the androgen known to contribute to male AGA. While oral finasteride and oral dutasteride share a few key benefits, they are both unique drugs with slightly different purposes and effects.

Between oral finasteride and oral dutasteride, oral finasteride is the older drug. Oral finasteride was developed in the 1970s and received FDA approval as a treatment for benign prostatic hyperplasia (BPH) in 1992. Oral finasteride was eventually approved for use as an AGA treatment in 1997 at a lower dose (1 mg) than the higher-dosed BPH treatment version of oral finasteride (5 mg). Dutasteride, on the other hand, was only patented in 1996 and became approved by the FDA as an oral treatment for BPH in 2001 at a dose of 0.5 mg.

Although oral dutasteride is approved as a treatment for AGA in some other countries, it still has not received FDA approval as a treatment for AGA in the United States.

In a study of 399 subjects, researchers found that oral dutasteride blocked 98.4%+/−1.2% of DHT at a 5 mg daily dose, compared to 70.8+/−18.3% with the same dose of oral finasteride. See Clark, R. V. et al. "Marked Suppression of Dihydrotestosterone in Men with Benign Prostatic Hyperplasia by Dutasteride, a Dual 5α-Reductase Inhibitor." *J Clin Endocrinol Metab* (2004) 89(5): 2179-84. This study was conducted on people suffering from BPH, meaning it used far higher doses of oral dutasteride and oral finasteride than the doses used to treat hair loss. Still, it shows that oral dutasteride is, milligram for milligram, more effective at lowering DHT than oral finasteride. In fact, even 0.5 mg daily dose of dutasteride blocked 94.7+/−3.3% of DHT, i.e., even at 10-fold lower dosing, dutasteride blocked DHT considerably more effectively than finasteride. It also shows that oral dutasteride is more consistent at blocking DHT than oral finasteride. The level of variability for the oral dutasteride group was +/−1.2%, showing an almost total elimination of DHT, with far less variation between patients than the +/−18.3% of the oral finasteride group. Study data also shows that oral dutasteride is more effective at promoting hair growth in people with male AGA than finasteride.

A 2006 study of 416 men shows that oral dutasteride produced better hair count results than oral finasteride over a period of 12 to 24 weeks. See Olsen, E. et al. 2006, supra. The researchers used an expert panel and before and after photographs to compare and verify the effects of the two drugs.

Unfortunately, systemic administration of 5-α reductase inhibitors is not recommended for the treatment or prevention of alopecia in patients receiving chemotherapy, or in women with breast cancer and endocrine therapy-associated alopecia, due to safety concerns, as the drug has been shown to increase serum estrogen levels in these patients (see, e.g., Rozner et al., Breast Cancer Res Treat. 2019; 174:15 (2019)).

New therapies are needed for selectively delivering inhibitors for 5-α reductase into the dermis of a subject, while limiting systemic exposure that can produce side effects that can be particularly serious in subjects suffering from ETIA.

SUMMARY OF THE INVENTION

The present features topical dutasteride emulsions for local delivery of dutasteride. The emulsions of the invention can deliver dutasteride to the dermis of a subject in amounts that ameliorate hair loss without exposing the subject to any significant deleterious systemic dutasteride exposure. The emulsions are of particular utility for the treatment of hair loss secondary to endocrine therapy in patients with breast cancer (Endocrine Therapy-Induced Alopecia or ETIA).

In a first aspect, the invention features an emulsion including:
  (i) from 0.025% to 0.20% (w/w) dutasteride;
  (ii) 3.0±0.15% (w/w) glycerin;
  (iii) 4.0±0.20% (w/w) oleyl alcohol;
  (iv) 20.45±1.0% (w/w) isopropyl myristate;
  (v) 24.00±1.2% (w/w) diethyl sebacate;
  (vi) 1.50±0.08% (w/w) steareth-2 (e.g., Brij® S2);
  (vii) 2.00±0.1% (w/w) steareth-21 (e.g., Brij® S721);
  (viii) 1.00±0.05% (w/w) cetearyl alcohol; and
  (ix) water to make 100% (w/w).

The invention further features an emulsion including:
  (i) from 0.025% to 0.20% (w/w) dutasteride;
  (ii) 5.0±0.25% (w/w) glycerin;
  (iii) 20.0±1.0% (w/w) diisopropyl adipate;
  (iv) 15.0±0.75% (w/w) medium chain triglycerides;
  (v) 7.3±0.35% (w/w) isopropyl palmitate;
  (vi) 3.00±0.15% (w/w) emulsifier formed from glyceryl stearate and PEG 100 stearate (e.g., Arlacel™ 165);
  (vii) 0.50±0.025% (w/w) sorbitan monostearate;
  (viii) 3.00±0.15% (w/w) cetearyl alcohol; and
  (ix) water to make 100% (w/w).

The invention further features an emulsion including:
  (i) from 0.025% to 0.20% (w/w) dutasteride;
  (ii) 5.0±0.25% (w/w) glycerin;
  (iii) 9.0±0.45% (w/w) olive oil;
  (iv) 15.0±0.75% (w/w) medium chain triglycerides;
  (v) 20.0±1.0% (w/w) diisopropyl adipate;
  (vi) 5.00±0.25% (w/w) emulsifier formed from ceteareth-20 and cetearyl alcohol (e.g., Promulgen™ D);
  (vii) 0.50±0.025% (w/w) benzyl alcohol;
  (viii) 0.50±0.025% (w/w) stearalkonium chloride; and
  (ix) water to make 100% (w/w).

In particular embodiments of the above emulsions, the emulsion may further include a thickener, an emollient, a pH adjuster, a preservative, and/or a conditioning agent, each, when present, in an amount of less than 0.5% (w/w).

In certain embodiments of the above emulsions, the emulsion includes from 0.025% to 0.15% (w/w) dutasteride. In some embodiments, the emulsion includes 0.025%, 0.050±0.0025%, 0.10±0.005%, 0.15±0.0075%; or 0.20% (w/w) dutasteride.

In certain embodiments, the emulsion is dermis-targeting.

The invention further features a method for ameliorating hair loss on the scalp of a human subject, comprising: a) providing an emulsion of the invention; and b) topically applying the emulsion to the scalp of the subject in an amount and for a duration sufficient to ameliorate hair loss; wherein amelioration of hair loss comprises an increase in scalp hair density, hair thickness, or scalp coverage. In particular embodiments, the human subject suffers from a condition selected from the group consisting of androgenetic alopecia (AGA), alopecia areata, and Endocrine Therapy-Induced Alopecia (ETIA). The ETIA can be hair loss secondary to endocrine therapy for breast cancer. The emulsion can be applied to scalp in an area comprising the frontal, central, vertex regions, or a combination thereof of the scalp.

An increase in scalp hair density, hair thickness, or scalp coverage in the human subject receiving the emulsion as compared to an untreated individual is indicative of ameliorating hair loss on the scalp of the human subject.

As used herein, unless otherwise stated, the singular forms "a," "an," and "the" include plural reference. Thus, for example, a reference to "a protein" includes a plurality of protein molecules.

As used herein, the term "about" in quantitative terms refers to plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

As used herein the term "dermis-targeting" refers to a formulation that when tested in the In Vitro Permeation Testing (IVPT) skin test of Example 6 produces an average ratio of dutasteride in the dermis relative to the epidermis at 24 hours of greater than 1.0, 1.5, or 2.0. Desirably, the dermis-targeting also produces little or no observable diffusion beyond the dermis in the IVPT skin test of Example 6 at 4 hours, 8 hours, and 24 hours.

As used herein the term "modulating hair growth" refers to an increase or decrease of hair count, hair thickness, or hair structure in scalp or face.

As used herein the term "therapeutically effective amount" is a sufficient to contribute to the treatment, prevention, or reduction of a symptom or symptoms of a disease. A reduction of a symptom or symptoms (and grammatical equivalents of this phrase) means decreasing of the severity or frequency of the symptom(s), or elimination of the symptom(s).

As used herein, the amount of dutasteride, when expressed as "%" refers to % (w/w) unless otherwise indicated.

As used herein, the phrase "pharmaceutically acceptable" is used with reference to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Other features and advantages of the invention will be apparent from the following Detailed Description, and the claims.

BRIEF DESCRIPTION OF THE DRAWINGS

FIG. 1 is an image depicting a hair follicle within the dermis and epidermis, and the tissue space of the dermis targeted by the formulations of the invention.

DETAILED DESCRIPTION OF THE INVENTION

The invention features topical emulsions of the 5-α reductase inhibitor dutasteride. The emulsion formulations can be useful for the treatment of hair loss secondary to endocrine therapy in patients with breast cancer (Endocrine Therapy-Induced Alopecia or ETIA). The emulsion formulations of the invention can produce an improved safety profile as they are able to selectively target the dermis without exposing the subject to any significant deleterious systemic dutasteride exposure, thereby minimizing the risk of systemic side effects in the subject.

Dutasteride is chemically designated as (5α, 17β)-N-{2,5 bis(trifluoromethyl)phenyl}-3-oxo-4-azaandrost-1-ene-17-carboxamide. The empirical formula of dutasteride is $C_{27}H_{30}F_6N_2O_2$, representing a molecular weight of 528.53 kDa. Dutasteride is a selective inhibitor of both the type 1 and type 2 5α-reductase isoenzymes, an intracellular enzyme that converts testosterone to dihydrotestosterone (DHT).

Additionally, dutasteride may be more effective than another known type 1 5α-reductase inhibitor, finasteride, since dutasteride inhibits both type 1 and type 2 5α-reductase isoenzymes.

EXAMPLES

The following examples are put forth to provide those of ordinary skill in the art with a description of how the compositions and methods described herein may be used, made, and evaluated, and are intended to be purely exemplary of the invention and are not intended to limit the scope of what the inventors regard as their invention.

Example 1

Topical Lotion Formulation Comprising Dutasteride

An emulsion formulation containing 0.05% w/w dutasteride was prepared as follows.

| Phase | Ingredients | % w/w | Category |
|---|---|---|---|
| A | Sterile Water for Irrigation | 42.20 | Aqueous solvent |
|   | Glycerin | 3.00 | Humectant |
|   | Methylparaben | 0.18 | Preservative |
| B | Carbopol 974P Polymer | 0.10 | Thickener |
| C | Oleyl Alcohol | 4.00 | Solvent |
|   | Isopropyl Myristate | 20.45 | Emollient |
|   | Diethyl Sebacate | 24.00 | Solvent |
|   | Dutasteride | 0.05 | API |
| D | Propylparaben | 0.02 | Preservative |
|   | Brij ® S2 | 1.50 | Emulsifier |
|   | Brij ® S721 | 2.00 | Emulsifier |
|   | Cetearyl Alcohol | 1.00 | Thickener |
| E | Sterile Water for Irrigation | 0.50 | Aqueous solvent |
| F | 10% NaOH Solution | 0.16 (pH 5.5-6.0) | pH adjuster |
| G | Sterile Water for Irrigation | ca. 0.84 | Aqueous solvent |
|   | Total | 100.00 | |

The components of Phase A were combined in the main manufacturing vessel and heated to 70-75° C., if necessary, to dissolve methylparaben. Phase B was sprinkled into the main vessel and mixed until no fish eyes were present. The main vessel was then heated until 75-80° C. The components of Phase C were combined in a separate vessel and homogenized until a solution was obtained. The components of Phase C were heated to 75-80° C., if necessary, to dissolve the dutasteride. The components of Phase D were added to Phase C while heating to 75-80° C. and mixed until Phase D was completely melted. Phases C+D were added to the main manufacturing vessel at 75-80° C. with homogenization until the oil phase was fully incorporated. Phase E was used to rinse the Phases C+D vessel. The main manufacturing vessel as cooled to ≤30° C. Phase F was used to neutralize the batch to pH 5.5-6.0. Phase G was added to the main manufacturing vessel in an amount sufficient such that the total was 100% w/w.

Formulations containing 0.025% (w/w), 0.10% (w/w), 0.15% (w/w), and 0.20% (w/w) dutasteride were also prepared. Varying the concentration of dutasteride within 0.025 to 0.20% (w/w) did not interfere with the formulation of homogenous phases within the resulting emulsion.

Example 2

Topical Lotion Formulation Comprising Dutasteride

An emulsion formulation containing 0.05% w/w dutasteride was prepared as follows.

| Phase | Ingredients | % w/w | Category |
|---|---|---|---|
| A | Sterile Water for Irrigation | 44.65 | Aqueous solvent |
|   | Sodium Hyaluronate | 0.10 | Humectant |

-continued

| Phase | Ingredients | % w/w | Category |
|---|---|---|---|
| B | Glycerin | 5.00 | Humectant |
|   | Xanthan Gum | 0.20 | Thickener |
| C | Methylparaben | 0.18 | Preservative |
| D | Diisopropyl Adipate | 20.00 | Solvent |
|   | Dutasteride | 0.05 | API |
| E | Medium Chain Triglycerides | 15.00 | Solvent |
|   | Isopropyl Palmitate | 7.30 | Emollient |
| F | Arlacel ™ 165 | 3.00 | Emulsifier |
|   | Sorbitan Monostearate | 0.50 | Emulsifier |
|   | Cetearyl Alcohol | 3.00 | Thickener |
|   | Propylparaben | 0.02 | Preservative |
| G | Sterile Water for Irrigation | ca. 1.00 | Aqueous solvent |
| H | Sterile Water for Irrigation | q.s. to 100 | Aqueous solvent |
|   | Total | 100.00 | |

The components of Phase A were combined in the main manufacturing vessel with high agitation until a homogeneous gel was obtained. The components of Phase B were combined in a separate vessel. Phase B was added to the main manufacturing vessel and mixed until uniformly dispersed. Phase C was added to the main manufacturing vessel and mixed until dissolved. The main manufacturing vessel was then heated to 70-75° C. Phase D was combined in a separate vessel with homogenization until a solution was obtained. The phase was heated to 70-75° C. if necessary to dissolve the dutasteride. The components of Phase E were added to Phases D one at a time until a solution was obtained. Phase F was added to Phases D+E while heating to 70-75° C. until Phases D+E+F were completely melted. Phases D+E+F were added to the main manufacturing vessel at 70-75° C. with homogenization until the oil phase was fully incorporated. Phase G was used to rinse the Phases D+E+F vessel. The main manufacturing vessel was cooled down to 30° C. Phase H was added to the main manufacturing vessel in an amount sufficient such that the total was 100% w/w.

Example 3

Topical Lotion (Conditioner) Formulation Comprising Dutasteride

An emulsion formulation containing 0.05% w/w dutasteride was prepared as follows.

| Phase | Ingredients | % w/w | Category |
|---|---|---|---|
| A | Sterile Water for Irrigation | 35.55 | Aqueous solvent |
|   | Stearalkonium Chloride | 0.50 | Emulsifier |
|   | Methylparaben | 0.18 | Preservative |
|   | Glycerin | 5.00 | Humectant |
| B | Olive Oil | 9.00 | Emollient |
|   | Benzyl Alcohol | 0.50 | Preservative |
|   | Medium Chain Triglycerides | 15.00 | Solvent |
|   | Diisopropyl Adipate | 20.00 | Solvent |
|   | Dutasteride | 0.05 | API |
| C | Promulgen ™ D | 5.00 | Emulsifier |
|   | Propylparaben | 0.02 | Preservative |
| D | Sterile Water for Irrigation | 1.00 | Aqueous solvent |
| E | Sterile Water for Irrigation | 8.00 | Aqueous solvent |
|   | Polyquaternium-10 | 0.20 | Conditioning agent |

-continued

| Phase | Ingredients | % w/w | Category |
|---|---|---|---|
| F | Sterile Water for Irrigation | q.s. to 100 | Aqueous solvent |
|   | Total | 100.00 | |

The components of Phase A were combined in the main manufacturing vessel and heated to 70-75° C., and mixed until uniform. The components of Phase B were combined in a separate vessel with homogenization until a solution was obtained. The components of Phase B were heated to 70-75° C., if necessary, to dissolve the dutasteride. The components of Phase C were added to Phase B while heating to 70-75° C., and mixed until Phase C was completely melted and incorporated. Phases B+C were added to the main manufacturing vessel at 70-75° C. with homogenization and mixed until the oil phase was fully incorporated. Phase D was used to rinse the Phases B+C vessel. The main manufacturing vessel was cooled to 40° C. The components of Phase E were combined in a separate vessel, then added to the main manufacturing vessel and mixed until uniform. The main manufacturing vessel was cooled to 30° C. Phase F was added to the batch in an amount sufficient such that the total was 100% w/w.

Example 4

Topical Gel Formulation Comprising Dutasteride

A gel formulation containing 0.05% w/w dutasteride was prepared as follows.

| Phase | Ingredients | % w/w | Category |
|---|---|---|---|
| A | Dehydrated Alcohol | 47.92 | Solvent |
|   | Propylene Glycol | 50.00 | Solvent |
|   | Dutasteride | 0.05 | API |
| B | Carbopol 980 NF, Polymer | 2.03 | Thickener |
| C | Dehydrated Alcohol | q.s. to 100 | Solvent |
|   | Total | 100.00 | |

The components of Phase A were combined in the main manufacturing vessel until a solution was obtained. Phase B was slowly added to the main manufacturing vessel with mixing until a homogenous gel was obtained. Phase C was added to the main manufacturing vessel in an amount sufficient such that the total was 100% w/w.

Example 5

Topical Gel Formulation Comprising Dutasteride

A gel formulation containing 0.05% w/w dutasteride was prepared as follows.

| Phase | Ingredients | % w/w | Category |
|---|---|---|---|
| A | Propylene Glycol | q.s. to 100 (72.95) | Solvent |
| | Transcutol ® P | 20.00 | Solvent |
| | Diethyl Sebacate | 3.00 | Emollient |
| | Dutasteride | 0.05 | API |
| B | Sepineo P 600 | 4.00 | Thickener |
| | Total | 100.00 | |

The components of Phase A were combined in the main manufacturing vessel until a solution was obtained. Phase B was added to the main manufacturing vessel with homogenization and mixed until a uniform gel was obtained.

Example 6

In Vitro Permeation Testing (IVPT)

Topical formulations of dutasteride were evaluated in an In Vitro Permeation Testing (IVPT) skin test to assess the effect of the formulation on the distribution of dutasteride into layers of skin (i.e., the epidermis and the dermis), and to assess the risk of systemic exposure for each formulation.

Five formulations of topical 0.05% dutasteride were selected for IVPT:
(1). Formulation 1: dutasteride Lotion, 0.05% w/w (emulsion of Example 1),
(2). Formulation 2: dutasteride Lotion, 0.05% w/w (emulsion of Example 2),
(3). Formulation 3: dutasteride Lotion (Conditioner), 0.05% w/w (emulsion of Example 3),
(4). Formulation 4: dutasteride Gel, 0.05% w/w (gel of Example 4),
(5). Formulation 5: dutasteride Gel, 0.05% w/w (gel of Example 5), Amounts of dutasteride absorbed in epidermis and dermis layer and permeated into the receptor medium at each time point were analyzed and reported using a pig ear skin model. Pig (porcine) skin is a widely accepted analog for human skin in laboratory testing. The pig ear, specifically, has hairs and follicles present at locations and depths similar to the human hair-bearing skin.

Methods

Skin Model

Fresh pig ears were purchased from a local slaughterhouse. Pig ears with hair thickness and density like human hair were selected. Pig ear skin tissues (dorsal side) were surgically removed from the selected pig ears. Hairs were not trimmed. A thin layer of fat tissue was retained. Average thickness of the processed pig ear skin tissues was 938 µm. The thickness was measured using a digital snap-gage. The tissues after processing were stored at −20° C. until use.

Formulations

Formulations were stored at room temperature and used as received.

Skin Barrier Integrity Testing

After passing initial visual inspection, barrier integrity of the skin tissue was evaluated using transepidermal electrical resistance measurement (TEER measurement, Z value). Measurement as conducted using LCR meter at frequency of 100 Hz at room temperature. The measurement medium was 0.9% NaCl solution, using a pair of stainless-steel electrodes. The measurement was conducted on HTS cell with donor and receptor chamber filled with 0.9% NaCl solution and the electrodes submerged in the solution.

Prior to the screening study, TEER value for the skin tissue was evaluated. Six tissue samples were taken. TEER value (Z value) was measured. All reported Z values are net values after subtraction of the measurement medium blank (1.0 KOhms). It was found that large majority of the tissues had Z value 5.0 KOhms or greater. For those tissues with visible defects, the Z value was found in the range of 0.1-0.5 KOhms. Therefore, 5.0 KOhms was used as threshold value for the skin.

Skin integrity was measured before incubation at 32° C. Any tissue having Z value lower than 5.0 KOhms was discarded.

In Vitro Percutaneous Absorption and Penetration Study

The formulation screening study was carried out in a High-Throughput Screening (HTS) station. The skin samples (after washing with 1×PBS, pH 7.4) were mounted on diffusion cells in the HTS station. A total of 20 diffusion cells were used in the study. Each cell in the station has a diffusion area of 0.503 $cm^2$ (8 mm in diameter). Each individual cell is a static Franz-Cell type. The receptor chamber was filled with 3.0 mL of 4% BSA (Bovine Serum Albumin) in water supplemented with 0.02% gentamicin sulfate, which was vigorously and continuously mixed. The temperature was set at 32±0.1° C.

The tissue samples in the HTS cells were equilibrated at 32±0.1° C. for 1 hour before dosing.

The dosing level was set at 7.5 µL per cell. Each of the formulations was applied using a positive displacement pipette. The applied formulation was dosed on the tissue with great care so that the formulation was spread evenly, but the pipette tip didn't touch the skin surface to avoid potential damage to skin barrier. Each formulation was run in four replicates (N=4).

At time points 4 hr and 8 hr, entire receptor medium was collected and replaced with a fresh batch of receptor medium pre-incubated at 32° C. The samples collected from the receptor medium were processed and stored in a freezer until analysis.

At 24 hr, after removal of the skin tissue from the HTS Franz Cell, the tissue surface was wiped with Q-tip wetted with 1×PBS three times to remove the "unabsorbed and unpenetrated" API. The standard tape-stripping method was used to remove the remaining "unabsorbed and unpenetrated" API. The standard (validated) procedure is that the first two tape strips are counted as "unabsorbed and unpenetrated" API. The collected Q-tips and first two strips were discarded.

The tape-stripping cycle was continued for additional 15 times for each skin sample to remove stratum corneum (SC) layer completely. For each stripping cycle, all applied tapes/tissues were lined up on a Teflon plate. Then a hard rubber-lined roller was pressed against the tapes/tissues to apply equal pressure across all samples to ensure uniformity for each cycle and entire procedure. Then, the tape strip was removed in a quick motion from each tape/tissue pair. The collected 15-tape-strips were discarded.

After removal of the SC layer, epidermis and dermis layer were separated using a surgical scalpel. The epidermis/dermis surface was first wetted with distilled water to aid the separation. Surgical blade #21 was used to scrape off epidermis from dermis. Scraped-off epidermis was collected from the surgical blade by wiping with damp paper towels (about 1.5×1.5 cm in size). The paper towels were combined and soaked in 4.0 mL of DMSO/Acetonitrile 50/50 v/v for overnight at room temperature using an orbital shaker. The remaining dermis layer was cut into small pieces and extracted with 4.0 mL of DMSO/Acetonitrile 50/50 v/v for overnight at room temperature using an orbit shaker. The extracts were collected and ready for analysis. The receptor medium at 24 hr was collected for analysis.

LC-MS/MS Analysis

Dutasteride was detected by liquid chromatography tandem mass spectrometry (LC-MS/MS), specifically, HPLC analysis using a Shimadzu Prominence HPLC system with a Synergi Polar-RP, 2.5 µm, 100 Å, 2.0×50 mm column. Calibration curves were first performed for dutasteride in (a) 4% BSA with 0.02% Gentamycin Sulfate in Water and (b) in Pig Ear Skin Soaked in DMSO/Acetonitrile 50/50 v/v, to calibrate the method for detection of dutasteride (a) in the receptor (systemic penetration model) and (b) in the dermis/epidermis (model for penetration of API into the active site).

Conclusion

Amount of Dutasteride in Receptor and Skin Layers

The results of the above tests are summarized in Table 1. Formulations with the highest detected amounts in the dermis without detection in the receptor fluid were deemed as the best performers.

TABLE 1

IVPT Data and Observed Ratio of Dermis to Epidermis Dutasteride Concentrations

| Collection Point | Run 1 (ng) | Run 2 (ng) | Run 3 (ng) | Run 4 (ng) | Average |
|---|---|---|---|---|---|
| Formulation 1 | | | | | |
| Epidermis at 24 hr | 62.8 | 51.6 | 227.6 | 33.5 | 93.9 |
| Dermis at 24 hr | 159.2 | 228.0 | 552.0 | 31.9 | 242.8 |
| Ratio Dermis/Epidermis | 2.5 | 4.4 | 2.4 | 1.0 | 2.6 |
| Formulation 2 | | | | | |
| Epidermis at 24 hr | 98.0 | 50.0 | 58.4 | 20.5 | 56.7 |
| Dermis at 24 hr | 254.0 | 52.8 | 35.1 | 39.6 | 95.4 |
| Ratio Dermis/Epidermis | 2.6 | 1.1 | 0.6 | 1.9 | 1.7 |
| Formulation 3 | | | | | |
| Epidermis at 24 hr | 70.0 | 32.0 | 353.6 | 71.2 | 131.7 |
| Dermis at 24 hr | 224.4 | 27.1 | 820.0 | 74.4 | 286.5 |
| Ratio Dermis/Epidermis | 3.2 | 0.8 | 2.3 | 1.0 | 2.2 |
| Formulation 4 | | | | | |
| Epidermis at 24 hr | 226.4 | 416.0 | 274.4 | 480.0 | 349.2 |
| Dermis at 24 hr | 86.8 | 173.2 | 75.6 | 343.6 | 169.8 |
| Ratio Dermis/Epidermis | 0.4 | 0.4 | 0.3 | 0.7 | 0.5 |
| Formulation 5 | | | | | |
| Epidermis at 24 hr | 420.0 | 256.4 | 416.0 | 724.0 | 454.1 |
| Dermis at 24 hr | 110.4 | 258.4 | 266.8 | 576.0 | 302.9 |
| Ratio Dermis/Epidermis | 0.3 | 1.0 | 0.6 | 0.8 | 0.7 |

Emulsion formulations 1-3 and gel formulation 4 produced no dutasteride in the receptor medium at any time point during the assay, demonstrating that these formulations exhibit a very low risk of producing any significant deleterious systemic dutasteride exposure if administered to a subject. In contrast, formulation 5 was observed to permeate through to the receptor medium at 24 hr (1.6 ng observed), suggesting that formulation 5 was most likely to produce systemic dutasteride exposure if administered to a subject.

Formulation 4 (dutasteride gel, 0.05% w/w of Example 4) and Formulation 5 (dutasteride gel, 0.05% w/w of Example 5) exhibited poor selectivity for the dermis, producing an average ratio of dutasteride in the dermis relative to the epidermis of 0.5 and 0.7, respectively.

In contrast, all three of the emulsion formulations 1-3, exhibited selectivity for the dermis, producing an average ratio of dutasteride in the dermis relative to the epidermis of 2.2 (dutasteride emulsion, 0.05% w/w of Example 3), 1.7 (dutasteride emulsion, 0.05% w/w of Example 2), and 2.6 (dutasteride emulsion, 0.05% w/w of Example 1).

Among the formulations selectively targeting the dermis, emulsion formulations 1 and 3 produced the highest dermis tissue concentrations at 242.8 ng and 286.5 ng, respectively.

Example 7

Treatment of Women Suffering from Hair Loss Secondary to Endocrine Therapy in Patients with Breast Cancer Two randomized, parallel-group studies can be conducted. Group I: 20 women suffering from hair loss secondary to endocrine therapy in patients with breast cancer can receive 0.5 mg of dutasteride in an emulsion formulation of one of Examples 1-3, applied to the affected area of the scalp once a day (q.d.) or twice a day (b.i.d) for at least 4 weeks, alternatively at least 8 weeks, alternatively at least 12 weeks, alternatively at least 16 weeks.

Group 2 may receive a placebo without the dutasteride applied to the affected area of the scalp once a day (q.d.) or twice a day (b.i.d) for at least 1 week, alternatively up to 12 weeks.

For each of the groups, hair thickness increase, target area hair count (TAHC), hair growth assessment (HGA), target area hair width (TAHW), scalp coverage, hair structure, and target area hair density (TAHD) can be measured.

An increase in hair thickness, target area hair count (TAHC), target area hair width (TAHW), scalp coverage, hair structure, or target area hair density (TAHD) in Group 1 individual as compared to Group 2 individuals is indicative of a positive response to the topical treatment with dutasteride to alopecia.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. Other embodiments are within the claims.

The invention claimed is:

1. A dermis-targeting emulsion comprising:
   (i) from 0.025% to 0.20% (w/w) dutasteride;
   (ii) 3.0±0.15% (w/w) glycerin;
   (iii) 4.0±0.20% (w/w) oleyl alcohol;
   (iv) 20.45±1.0% (w/w) isopropyl myristate;
   (v) 24.00±1.2% (w/w) diethyl sebacate;
   (vi) 1.50±0.08% (w/w) steareth-2;
   (vii) 2.00±0.1% (w/w) steareth-21;
   (viii) 1.00±0.05% (w/w) cetearyl alcohol; and
   (ix) water to make 100% (w/w).

* * * * *